(12) United States Patent
Baccelli et al.

(10) Patent No.: US 7,316,684 B1
(45) Date of Patent: Jan. 8, 2008

(54) MULTIAXIAL CONNECTION FOR OSTEOSYNTHESIS

(75) Inventors: Christian Baccelli, Ayguemorte les Graves (FR); Frédéric Conchy, Saint Medard d'Eyrans (FR); Fabien Gauchet, Duvy (FR); Régis Le Couedic, Cestas (FR); Denis Pasquet, Bordeaux (FR); Pierre Henri Saint Martin, Pessac (FR); Michéle Turner-Domergue, Pessac (FR); Cécile Vienney, Bordeaux (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 10/031,563

(22) PCT Filed: Jul. 20, 2000

(86) PCT No.: PCT/FR00/02085

§ 371 (c)(1),
(2), (4) Date: Apr. 24, 2002

(87) PCT Pub. No.: WO01/06940

PCT Pub. Date: Feb. 1, 2001

(30) Foreign Application Priority Data

Jul. 22, 1999 (FR) .................................. 99 09524

(51) Int. Cl.
*A61B 17/56* (2006.01)
*A61B 17/58* (2006.01)
(52) U.S. Cl. ........................................................ 606/61
(58) Field of Classification Search .................. 606/61, 606/71, 72, 73, 53, 60
See application file for complete search history.

(56) References Cited

U.S. PATENT DOCUMENTS

| 5,429,639 | A | * | 7/1995 | Judet ............................ 606/61 |
| 5,549,608 | A | * | 8/1996 | Errico et al. ................... 606/61 |
| 5,575,792 | A | * | 11/1996 | Errico et al. ................... 606/61 |
| 5,584,834 | A | * | 12/1996 | Errico et al. ................... 606/61 |
| 5,733,285 | A | * | 3/1998 | Errico et al. ................... 606/61 |
| 5,817,094 | A | * | 10/1998 | Errico et al. ................... 606/61 |
| 5,882,350 | A | * | 3/1999 | Ralph et al. ................... 606/61 |
| 6,010,503 | A | * | 1/2000 | Richelsoph et al. ........... 606/61 |
| 6,132,432 | A | * | 10/2000 | Richelsoph ................... 606/61 |
| 6,280,442 | B1 | * | 8/2001 | Barker et al. ................. 606/60 |
| 6,355,040 | B1 | * | 3/2002 | Richelsoph et al. ........... 606/61 |
| 6,368,320 | B1 | * | 4/2002 | Le Couedic et al. .......... 606/61 |
| 6,371,957 | B1 | * | 4/2002 | Amrein et al. ................. 606/61 |

FOREIGN PATENT DOCUMENTS

| DE | 299 03 342 | 6/1999 |
| FR | 2 771 918 A1 | 6/1999 |
| WO | 97/02786 A1 | 1/1997 |
| WO | 98/32386 A1 | 7/1998 |

* cited by examiner

*Primary Examiner*—Pedro Philogene
(74) *Attorney, Agent, or Firm*—Lerner, David, Littenberg, Krumholz & Mentlik, LLP

(57) ABSTRACT

A multiaxial connection osteosynthesis system for the spine having a bone anchor, a connector and a connecting member. The bone anchor may be implanted into a vertebral body with a connector being attached to a head of the bone anchor. The connector includes a seat for receiving the connecting member. As the connecting member is locked into position it causes walls of the connector to inwardly deform and lock the head of the bone anchor relative to the connector.

34 Claims, 4 Drawing Sheets

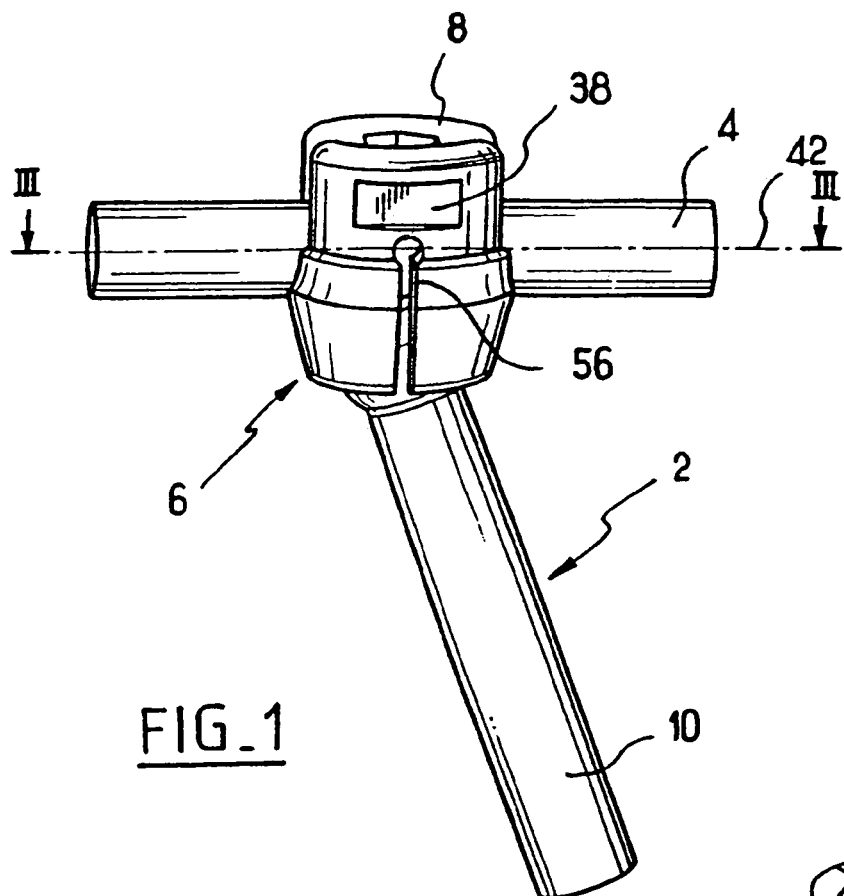
FIG_1
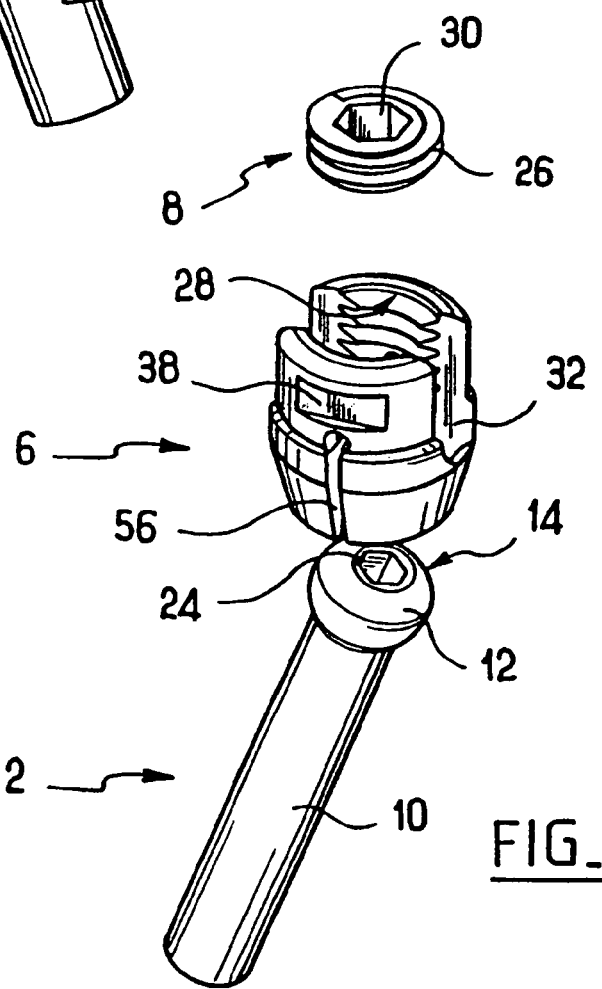
FIG_2

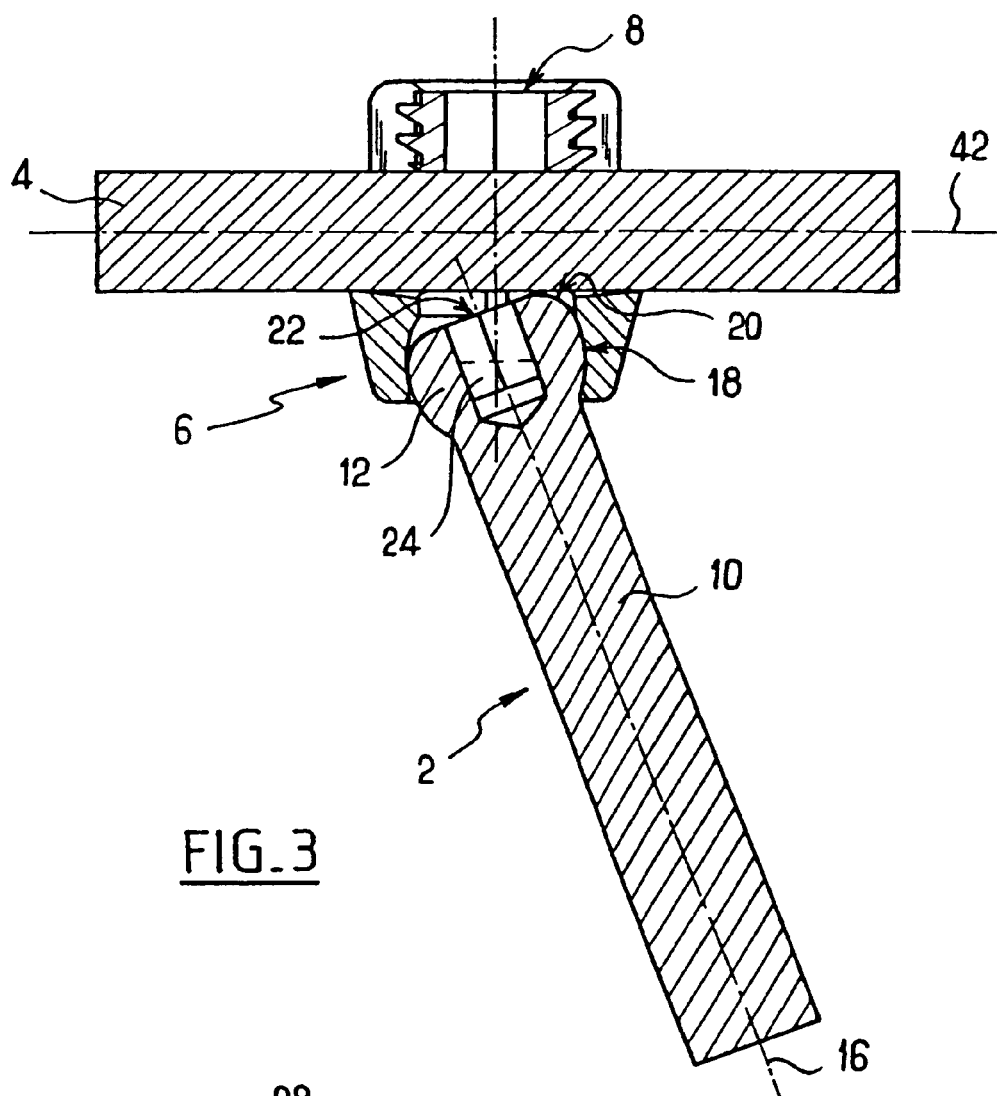
FIG. 3
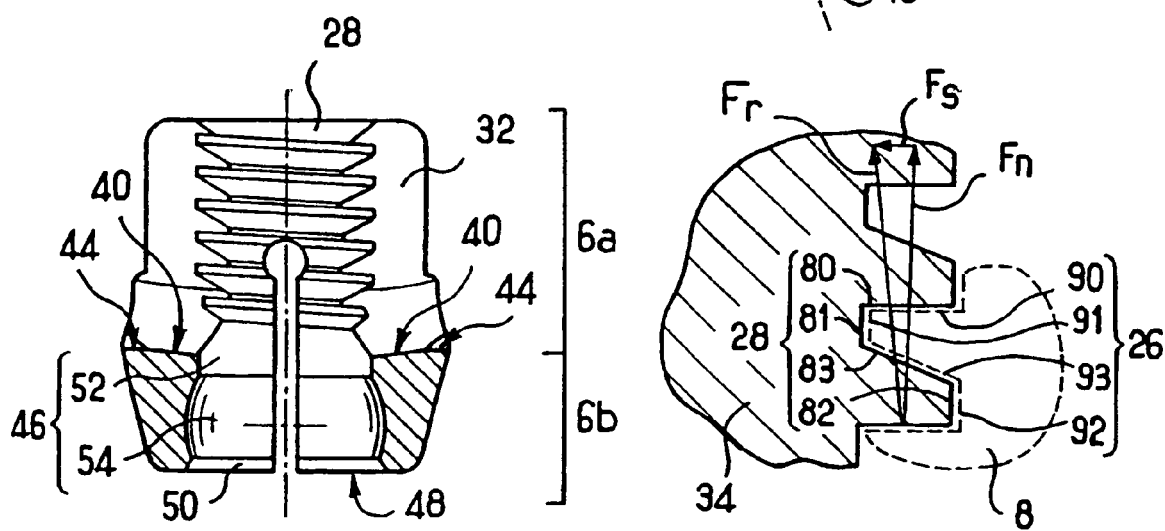
FIG. 6
FIG. 6a

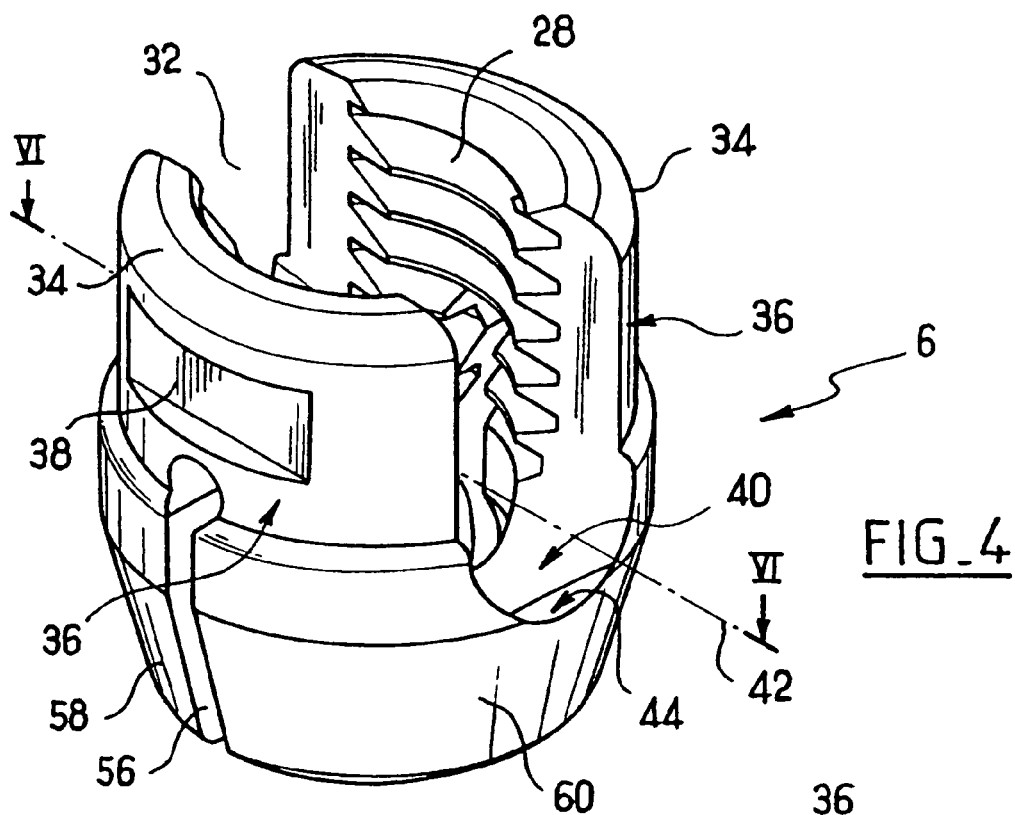
FIG_4
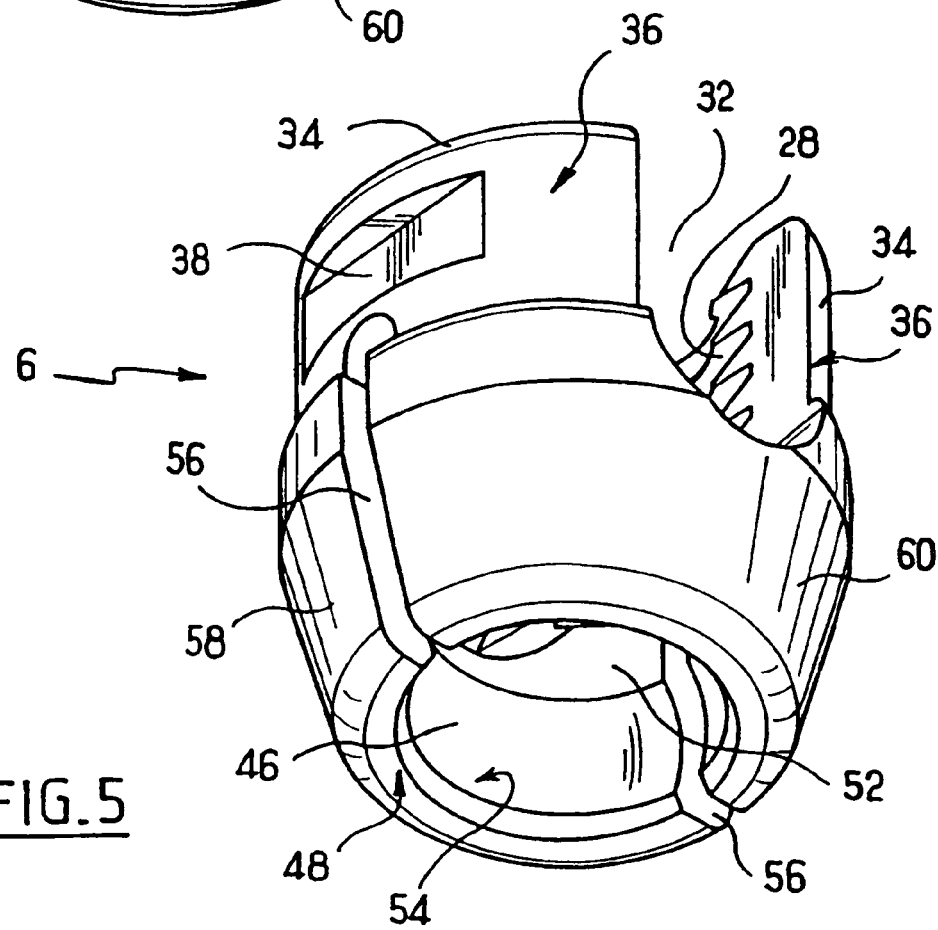
FIG_5

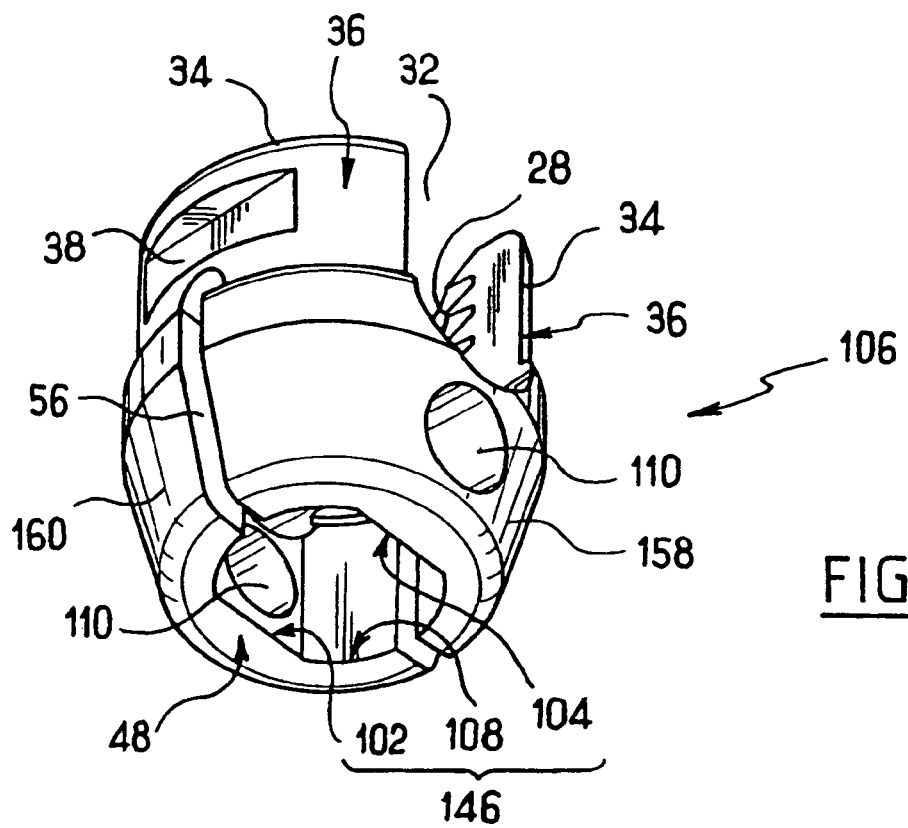
FIG_7
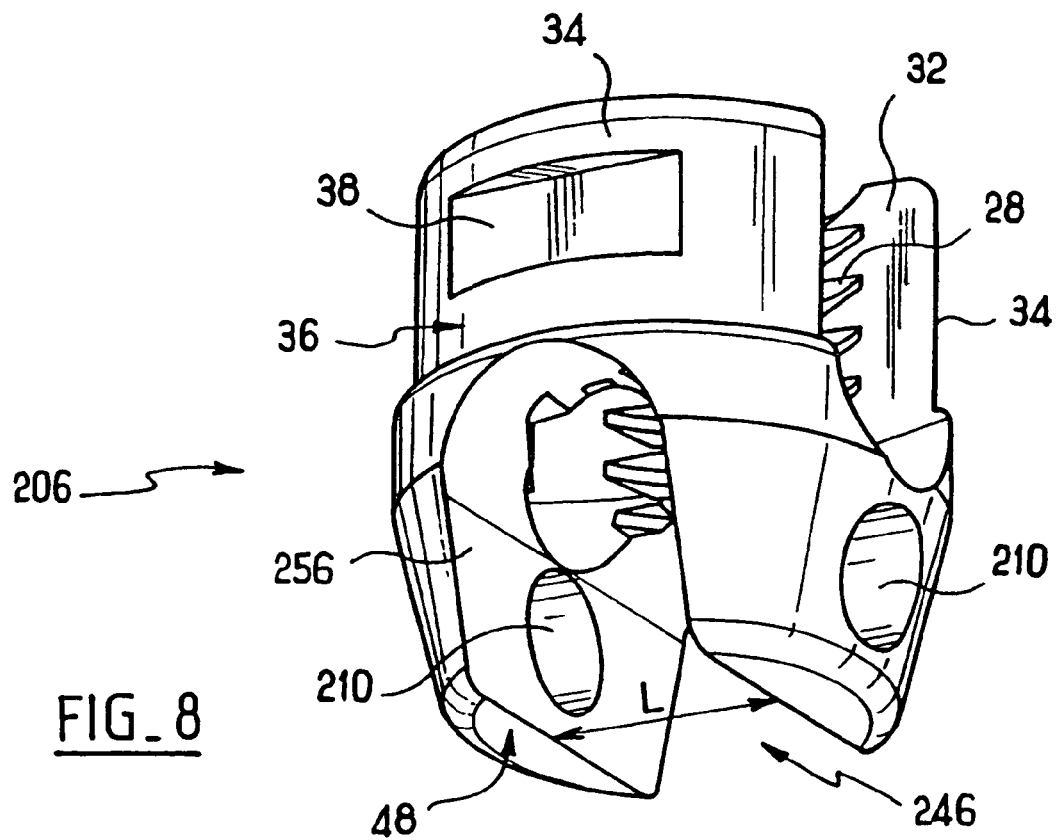
FIG_8

US 7,316,684 B1

MULTIAXIAL CONNECTION FOR OSTEOSYNTHESIS

BACKGROUND OF THE INVENTION

The present invention relates to a multiaxial connection osteosynthesis system, in particular for the spine.

In the context of surgery on the vertebral column, and in particular when using a posterior approach route, the surgeon is often confronted with the problems of misalignment of the anchor members and interference between anchor members on two adjacent vertebrae. This problem increases the operating time or prevents the surgeon from carrying out the desired procedure under the best possible conditions. The cause of this problem is that the coupling member located between the member connecting the various vertebrae and the anchor member implanted in the vertebra is rigidly connected to the anchor member.

Reference WO 97/02786 discloses a multiaxial connection between the members. The anchor member has a hemispherical head. The coupling member includes, in addition to means for receiving the member connecting the various vertebrae together, a split chamber in its bottom part adapted to receive the hemispherical head. The external surface of the coupling member includes a cone that is flared toward the bottom end. A clamping collar can be threaded over the top portion of the coupling member to bear on the conical portion. Before tightening, the coupling member is free to rotate relative to the anchor member. Locking in position is effected when tightening the member connecting the vertebrae together. The member bears on the clamping collar, while at the same time closes the receiving chamber on the hemispherical head of the anchor member.

The complexity of the positional locking mechanism, because of its large number of components, obliges the surgeon to carry out supplementary manipulations, and consequently increases the operating time.

An object of the present invention is to provide a multiaxial connecting device that is simple to use and requires only a small number of operations to complete assembly.

SUMMARY OF THE INVENTION

To achieve this object, the present invention provides a multiaxial connection osteosynthesis system, in particular for the spine, including a bone anchor member having a head, a connecting member, a connector having a first housing with a recess adapted to receive the head and a second housing adapted to receive the connecting member. The system further includes clamping means, i.e. a locking member such as, for example, an axially moveable screw, for clamping the connecting member in the second housing. The connector is arranged so that when the clamping means load the connecting member in the second housing, the connecting member loads ridges of the connector directly to reduce the dimension of the recess of the first housing and immobilize the head therein.

Thus the first deformable housing is closed onto the head. This reduces the number of components and therefore simplifies the use of the device.

The first housing may advantageously includes a chamber with a concave surface. The concave surface chamber is advantageously complementary to all or part of the convex surface of the head. The first housing advantageously includes a cavity adapted to receive part of the head.

The connector includes a slot in the first housing. Thus the first housing can have a more pronounced elastic deformability while inserting the head and while locking the device into position.

The head may advantageously include a spherical part.

The first housing advantageously includes a U-shaped opening having an axis and two branches at a distance from and facing each other. The slot is located preferably perpendicular to the axis of the U-shaped opening. The branches of the U-shaped opening may include have a screwthread. The clamping means may include a locking member adapted to engage between the branches of the U-shaped opening. The clamping means or locking element may additionally include a flange adapted to fit around the branches of the U-shaped opening. Accordingly, when clamping the nut, the flange prevents spreading of the branches of the U-shaped opening. The screwthread may have a face substantially perpendicular to the axis of the thread and oriented in a penetration direction of the clamping means on the connector.

Accordingly, during clamping, the face substantially perpendicular to the axis of the thread of the locking member comes into contact with the face of the branches of the U-shaped opening. The reaction force generated in this way is substantially parallel to the axis of the thread and this minimizes the radial reaction force. Otherwise the radial reaction force would spread apart the branches of the U-shaped opening.

BRIEF DESCRIPTION OF THE DRAWINGS

Other features and advantages of the present invention will become more apparent in the course of the following description of three preferred embodiments, which description is given by way of non-limiting examples. In the accompanying drawings:

FIG. 1 shows a partial perspective side view of a first embodiment of the present invention;

FIG. 2 shows an exploded perspective view of the system shown in FIG. 1;

FIG. 3 shows a cross-sectional view of the system shown in FIG. 1;

FIG. 4 is a top perspective view of the first embodiment of the present invention;

FIG. 5 is a bottom perspective view of the connector shown in FIG. 4;

FIG. 6 is a cross-sectional view of the connector shown in FIG. 4;

FIG. 6a is a diagrammatic sectional view of the Christmas tree thread of the connector shown in FIG. 4;

FIG. 7 is a bottom perspective view of a second embodiment of the present invention; and FIG. 8 is a bottom perspective view of a third embodiment of the present invention.

DETAILED DESCRIPTION

A first embodiment of the present invention is described with reference to FIGS. 1 to 6a.

The osteosynthesis system includes at least two vertebral anchor members 2, connecting means 4, such as a rod, extending between the anchor member 2 and the other anchor member (not shown) of the osteosynthesis system, a connector 6 adapted to be fitted to the member 2, and clamping means, i.e. a locking member 8 adapted to cooperate with the connector 6.

The vertebral anchor member 2, which in the preferred embodiment takes the form of a bone screw, may have a circular section cylindrical threaded body 10 carrying a bone thread (not shown). The preferred member 2 also may have a head 12 with a convex surface 14. The convex surface 14 has a surface of revolution whose axis coincides with the axis of the screw. The convex surface has a spherical lateral portion 18, a flat top portion 22, perpendicular to the axis of the screw, and a connecting fillet 20 between them, as shown in FIG. 3. The head 12 includes cavity 24 for operating the screw 2, here in the form of a hexagonal socket 24.

As shown in FIG. 2, the locking member 8 may be generally screw-shaped and have a thread 26 adapted to cooperate with the thread 28 on the connector 6, described hereinafter. The latter also includes socket 30 in the form of a hexagonal socket 30.

The connector 6 provides a coupling member between the bone screw 2 and the connecting rod 4. The general shape of the coupling member is that of a circular section cylinder. As shown in FIG. 6, it has a top portion 6a, for connecting to the rod 4 and a bottom portion 6b for connecting to the bone screw 2.

As shown in FIGS. 4 and 5, the top portion 6a of the coupling member 6 includes a U-shaped opening 32 which has an axis 42 and is delimited by two facing branches 34 at a distance from each other. The two branches 34 constitute two sectors of a common circular section cylinder forming the coupling member 6. The cylindrical external faces 36 of the branches 34 are coaxial and smooth. They can include grooves 38, for example, in the form of a notch on each of the branches 34. The grooves 38 have a flat bottom parallel to the axis 42 of the U-shaped opening 32. The grooves 38 are symmetrical mirror images of each other with respect to the median plane of the U-shaped opening 32. The cylindrical inside faces 28 of the branches are coaxial and threaded. Their thread is adapted to cooperate with that of the locking member 26.

The two threads 26 and 28 are complementary and are referred to as "Christmas tree" threads. As shown in FIG. 6, the thread 28 has a first face 80 substantially perpendicular to the axis of the thread. A second face 81 substantially parallel to the axis of the thread delimits the bottom of the thread. A third face 83 opposite the first face 80 and can be inclined in the direction of the axis relative to the direction of the first face 80. Lastly, a fourth face 82 located substantially parallel to the axis of the thread, delimits the crest of the thread. The thread 26 is substantially complementary to the thread 28. The thread 26 has a first face 90 parallel to and complementary to the face 80, a second face 91 substantially parallel to the axis of the thread delimiting the crest of the thread, a third face 93 substantially parallel to and complementary to the face 83, and a fourth face 92 substantially parallel to the axis of the thread delimiting the bottom of the thread. During clamping, the face 90 of the thread 28 comes into contact with the face 80 of the thread 26. The reaction force Fr generated in this way has a normal component Fn parallel to the axis of the threads and a transverse component Fs in the radial direction. The transverse component Fs may cause the branches 34 to spread during tightening of the locking member 8, but the particular shape of the threads 26, 28 previously referred to reduces the transverse component Fs and therefore reduces the spreading of the branches 34 during clamping.

In a plane perpendicular to the axis 42, the bottom 40 of the U-shaped opening is semicircular to receive the connecting rod 4, with a diameter equivalent to that of the connecting rod 4. On the other hand, the bottom 40 has a concavity in the median plane of the U-shaped opening 32 with a center of curvature situated on the same side as the portion 6a of the connector 6. Finally, the bottom 40 has ends 44 parallel to the axis 42, providing a seat to receive the connecting rod 4.

The bottom portion 6b of the connector 6 includes a housing 46 opening onto the bottom face 48 at an insertion orifice 50 and opening onto the bottom 40 of the U-shaped opening 32 at a communication orifice 52. The circular section insertion orifice 50 allows the head 12 of the bone screw 2 to be inserted into the housing 46. The housing 46 has a part-spherical bottom chamber 54 adapted to receive the head 12 of the bone screw 2. The shape of the bottom chamber 54 is complementary to the spherical lateral portion 18 of the convex surface 14 of the head 12. A slot 56 crosses the bottom part 6b diametrally. The slot 56 is perpendicular to the axis 42 of the U-shaped opening 32. It extends downward as far as the bottom face 48 of the connector 6 and upward until it opens onto the bottom 40 of the U-shaped opening 32. Thus the bottom part 6b is divided into two subparts 58 and 60 which are symmetrical mirror images of each other with respect to the median plane of the slot 56. The slot 56 facilitates clipping the head 12 into the coupling member 6 by facilitating deformation of the receiving space 46.

Prior to the procedure, each connector 6 is premounted by clipping it onto the head 12 of the bone screw 2. The bone screw is implanted in the patient using an instrument inserted into the cavity 24 via the communication orifice 52. When the screw 2 has been implanted, the connector 6 is free to rotate relative to the screw 2. The connector and the screw are connected together by a ball-and-socket connection formed by the head 12 and the bottom chamber 54. The rod 4 is fitted into the U-shaped opening 32 so that it rests on the ends 44 of the bottom 40. The locking member 8 is then engaged between the branches 34 of the opening 32 with the threads 26 and 28 interengaged with each other. The locking member 8 is then pressed against the rod 4 and the surgeon tightens the locking member 8. The locking member 8 bears on the rod 4. The rod 4 bears on the ends 44 of the bottom 40, which is then deformed because of the presence of the slot 56 perpendicular to the axis 42 of the opening 32, which is closed up as the two subparts 58 and 60 move toward each other. Consequently, the receiving space 46 and the chamber 54 are closed up onto the head 12 of the bone screw 2, locking the assembly in position, rigidly immobilizing the connector on the head of the bone screw.

In the second embodiment, shown in FIG. 7, the modifications relative to the first embodiment relate to the bottom part of the connector 106. The housing 146 no longer includes a spherical chamber, but instead is in the shape of a circular cylinder with two flats 102 and 104. The radius of the circular portion 108 can be equivalent to the radius of the head 12 of the bone screw 2. The two flats 102 and 104 are parallel to the slot 56. A circular section hole 110 perpendicular to the flats 102 and 104 passes completely and diametrally through the bottom part in the area of the flats and perpendicularly thereto. The diameter of the hole 110 is substantially equivalent to the width of the flats 102 and 104.

When the connector 106 is clipped to the head 12 of the bone screw 2, the head 12 locates in the holes 110, leaving free the ball-and-socket connection formed in this way.

The use of this embodiment is identical to that of the first embodiment during clamping, the deformation of the receiving space 146 by the movement toward each other of the two subparts 158 and 160 obliging the two flats 102 and 104 to move toward each other, thereby immobilizing the head 12 of the bone screw 2 in the holes 110.

In the third embodiment, shown in FIG. 8, the modifications relative to the previous embodiment relate to the bottom part of the connector 206. The housing 246 and the slot 256 are coincident, the slot 256 being the same width as the housing 246. The width L of the slot 256 is less than the diameter of the head 12 of the bone screw 2. As in the preceding embodiment, a circular section hole 210 passes completely through the bottom part of the connector 206 in the area of the flats and perpendicularly thereto, diametrally and perpendicularly to the walls of the slot 256. The diameter of the hole 210 is less than that of the spherical part 18 of the convex surface 14 of the head 12.

The clipping is effected in the same manner: the head 12 is accommodated in the holes 210, leaving free the ball-and-socket connection formed in this way.

The use of this embodiment is identical to that of the second embodiment. The locking in position is similar.

Of course, many modifications can be made to the invention without departing from the scope of the invention.

The anchor members can be hooks. The clamping means can include a ring or a flange adapted to be threaded over the branches of the U-shaped opening instead of or in addition to the locking member. In the latter case, the flange or ring can be connected to the locking member.

The thread cooperating with that of the branches can be on the flank, the branches being threaded on their outside face.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A multiaxial connection osteosynthesis system, for the spine, comprising a bone anchor member having a head, a connector having a first inwardly deformable portion adapted to receive said head and integral with a second portion, said second portion having a U-shaped opening having an open end remote from said first inwardly deformable portion and a seat, said seat being integrally formed with said connector, said open end adapted to receive a connecting member along an axis, said first and second portions extending along said axis, and a clamping means moveable along said axis for clamping said connecting member in said second portion, said clamping means being disposed within said U-shaped opening wherein said connector is arranged so that, when said clamping means loads said connecting member in said second portion in the direction of said axis, said connecting member loads said seat to inwardly deflect said first portion and immobilize said head therein.

2. The system according to claim 1 wherein said first inwardly deformable portion includes a chamber with a concave surface.

3. The system according to claim 1 wherein said first inwardly deformable portion includes a cavity adapted to receive part of said head.

4. The system according to claim 1 wherein said head has a spherical part.

5. The system according to claim 1, wherein said connector includes a slot in said first portion.

6. The system according to claim 5 wherein said U-shaped opening has an axis and two branches at a distance from and facing each other.

7. The system according to claim 6, wherein said slot is perpendicular to said axis of the U-shaped opening.

8. The system according to claim 7, wherein said clamping means include a locking member adapted to engage between said branches of said U-shaped opening.

9. The system according to claim 8, wherein said clamping means include a flange adapted to fit around said branches of said U-shaped opening.

10. The system according to claim 9, wherein said branches of said U-shaped opening have a screw thread.

11. The system according to claim 10, wherein said screw thread has a face substantially perpendicular to an axis of said screw thread and oriented in a penetration direction of said clamping means on said connector.

12. A multiaxial connection osteosynthesis system comprising:
 a bone anchor member having a head;
 a connecting member;
 a connector having a first housing with a recess adapted to receive said head and having an inwardly deformable portion connected to said first housing and a second housing having a U-shaped opening and a seat adapted to receive said connecting member, said seat including at least two raised ends and said seat being integrally formed with said connector, said U-shaped opening of second housing having an open end remote from said first housing, said open end being configured to receive said connecting member therein by movement of said connecting member along an axis toward said seat;
 a locking member moveable along said axis for exerting a force on said connecting member against said raised ends of said seat in said second housing wherein said raised ends apply a force against said first housing as said locking member clamps said connecting member, inwardly deforming said deformable portion thereby immobilizing said head therein.

13. The system according to claim 12, wherein said first housing includes a chamber having a concave surface.

14. The system according to claim 12, wherein said first housing includes a cavity adapted to receive part of said head.

15. The system according to claim 12, wherein said head has a spherical part.

16. The system according to claim 12, wherein said connector includes a slot located in said first housing.

17. The system according to claim 14, wherein said connector includes a slot located in said first housing.

18. The system according to claim 12, wherein said U-shaped opening has an axis and at least two branches, said branches separated by a distance from and facing each other.

19. The system according to claim 18, wherein said slot is perpendicular to said axis of said U-shaped opening.

20. The system according to claim 18, wherein said locking member is adapted to be engaged between said branches of said U-shaped opening.

21. The system according to claim 18, wherein said locking member includes a flange.

22. The system according to claim 20, wherein said locking member includes a flange.

23. The system according to claim 18, wherein said branches of said U-shaped opening have a screw thread.

24. The system according to claim 23, wherein said screw thread comprises a face substantially perpendicular to said axis of said thread and oriented in the penetration direction of said locking member on said connector.

25. A multiaxial connection osteosynthesis system comprising:
- a bone anchor having a head;
- a connecting member;
- a connector having a first housing with a recess for receiving said head of said bone anchor and a second housing having a U-shaped opening and having a seat adapted to engage said connecting member, said seat being integrally formed with said connector, said seat further having at least two raised ends and said first housing having walls separated by two slots, said slots extending from an exterior of said connector to said recess of said first housing, said U-shaped opening having an open end remote from said first housing and configured to receive said connecting member along an axis; and
- a locking member for clamping said connecting member on said seat in said second housing wherein an axial force applied by said locking member disposed within said U-shaped opening of said connector, said locking member along said axis causes said connecting member to engage said raised ends on said seat and deflect said walls of said first housing inwardly about said slots to cause said recess of said first housing to lock said head of said bone anchor within.

26. The system according to claim 25, wherein said first housing includes a chamber having a concave surface.

27. The system according to claim 25, wherein said first housing includes a cavity adapted to receive part of said head.

28. The system according to claim 25, wherein said head has a spherical part.

29. The system according to claim 25, wherein said connector includes a slot located in said first housing.

30. The system according to claim 25, wherein said U-shaped opening has an axis and at least two branches, said branches separated by a distance from and facing each other.

31. The system according to claim 30, wherein said slots are perpendicular to said axis of said U-shaped opening.

32. The system according to claim 30, wherein said locking member is adapted to be engaged between said branches of said U-shaped opening.

33. The system according to claim 30, wherein said locking member includes a flange.

34. The system according to claim 30, wherein said branches of said U-shaped opening have a screw thread.

* * * * *

UNITED STATES PATENT AND TRADEMARK OFFICE
CERTIFICATE OF CORRECTION

PATENT NO.        : 7,316,684 B1
APPLICATION NO.   : 10/031563
DATED             : January 8, 2008
INVENTOR(S)       : Baccelli et al.

It is certified that error appears in the above-identified patent and that said Letters Patent is hereby corrected as shown below:

At Column 1, line 63, "includes" should read -- include --.
At Column 2, line 10, "have" should be deleted after "may include".
At Column 3, line 43, after "80", please delete "and".
At Column 3, line 46, after "of the thread", please delete the comma.
At Column 6, line 29, after "opening of", please insert -- said --.
At Column 7, line 21, after "locking member", please insert -- is --.

Signed and Sealed this

Twelfth Day of January, 2010

David J. Kappos
*Director of the United States Patent and Trademark Office*